United States Patent [19]

Skallen

[11] Patent Number: 4,875,362
[45] Date of Patent: * Oct. 24, 1989

[54] METHOD AND APPARATUS FOR MEASURING THE VISCOSITY OF A MEDIUM

[75] Inventor: Bengt Skallen, Saffle, Sweden

[73] Assignee: Eur-Control Kalle AB, Sweden

[*] Notice: The portion of the term of this patent subsequent to Jul. 7, 2004 has been disclaimed.

[21] Appl. No.: 849,761

[22] Filed: Apr. 9, 1986

[30] Foreign Application Priority Data

Apr. 17, 1985 [SE] Sweden .................................. 8501892

[51] Int. Cl.⁴ ............................................. G01N 11/16
[52] U.S. Cl. ......................................................... 73/54
[58] Field of Search .................................. 73/54, 59, 60

[56]  References Cited

U.S. PATENT DOCUMENTS

| | | | |
|---|---|---|---|
| 2,696,735 | 12/1954 | Woodward | 73/59 |
| 2,837,913 | 6/1958 | Rich et al. | 73/59 |
| 2,839,915 | 6/1958 | Roth et al. | 73/59 |
| 2,973,639 | 3/1961 | Banks | 73/54 |
| 3,381,525 | 5/1968 | Kartluke et al. | 73/59 |
| 3,474,663 | 10/1969 | Whitmer et al. | 73/54 |
| 3,479,863 | 11/1969 | Kleiss | 73/54 |
| 3,734,119 | 5/1973 | Nudds | 73/54 |
| 3,769,088 | 3/1974 | Gustafsson et al. | 73/59 |
| 3,943,753 | 3/1976 | Simon | 73/59 |
| 4,148,215 | 4/1979 | Hofstetter, Jr. | 73/59 |
| 4,341,111 | 7/1982 | Husar | 73/59 |
| 4,602,505 | 7/1986 | Kanda et al. | 73/54 |
| 4,677,846 | 7/1987 | Lundberg | 73/63 |

FOREIGN PATENT DOCUMENTS

| | | | |
|---|---|---|---|
| 504882 | 7/1930 | Fed. Rep. of Germany | 73/59 |
| 15838 | 1/1984 | Japan | 73/54 |
| 851621 | 10/1960 | United Kingdom | 73/54 |
| 1233881 | 6/1971 | United Kingdom | 73/54 |

Primary Examiner—Hezron E. Williams
Attorney, Agent, or Firm—Ostrolenk, Faber, Gerb & Soffen

[57] ABSTRACT

The invention relates to a method and apparatus for measuring the viscosity of a medium with the aid of a blade (2) pivotally suspended such as to oscillate between two side walls (3, 4) in a measuring zone. The blade (2) is caused to pivot intermittently, with constant forces from an electromagnetic system (9) and a plunger coil (20), in the medium between the two fixed side walls (3, 4) which have a chief plane preferably extending parallel to, and in the same direction as the chief plane of the blade (2). The medium, which is in at least one first intermediate space between one side surface of the blade (2) and the side wall (3;4) facing it, being urged away in the direction of movement of the blade (2) simultaneously as new medium is sucked into at least one second intermediate space between the other side surface of the blade (2) and the other side wall (3;4) opposite thereto, a sheer force occurring when the medium is urged out from, or sucked into the measuring zone, and time measurement takes place when the free end (6) of the blade (2) traverses the distance (A-B;B-A) between the end positions, said time being a function of the sheer force, which in its turn is a function of the viscosity of the medium.

25 Claims, 1 Drawing Sheet

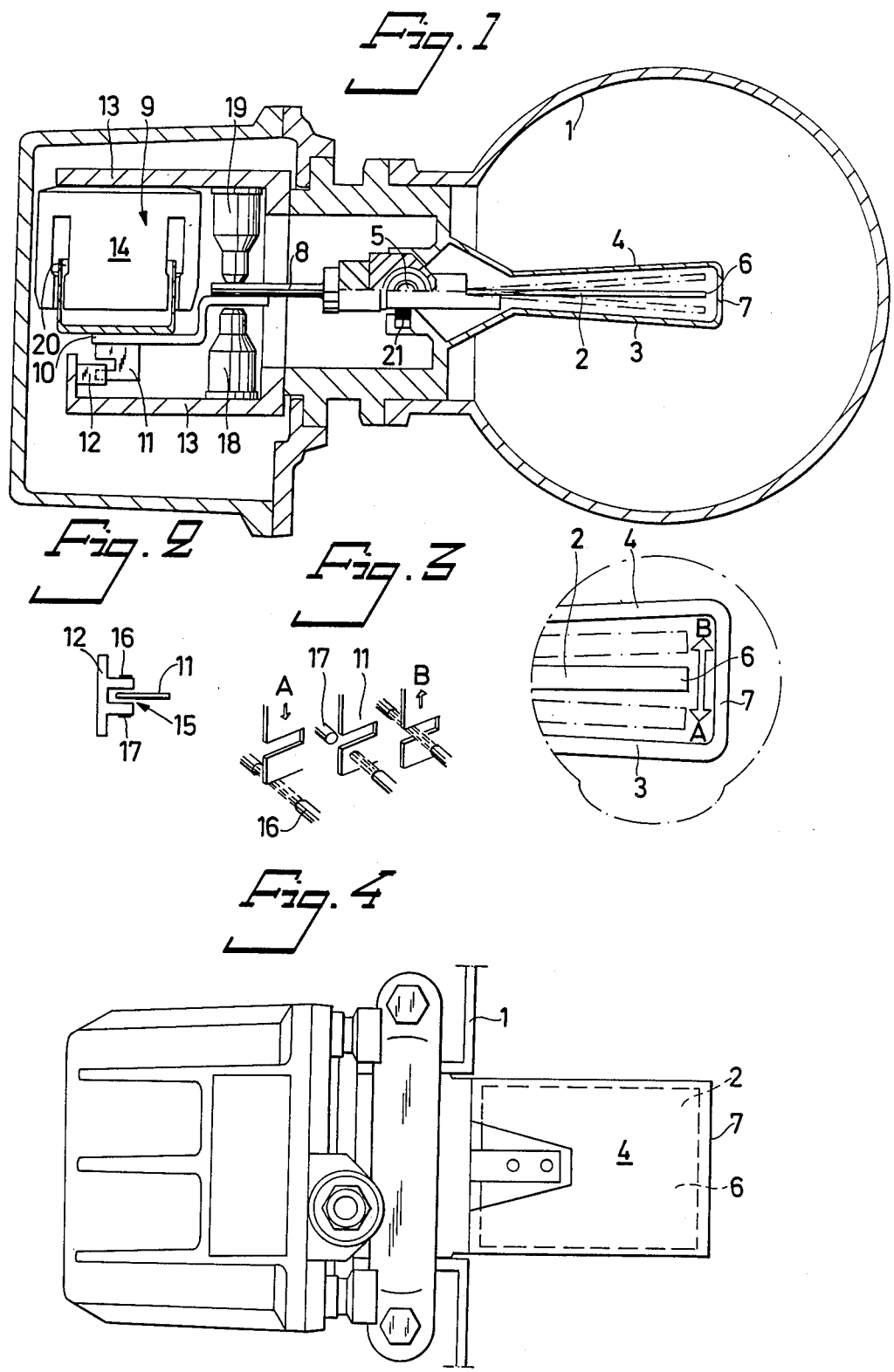

METHOD AND APPARATUS FOR MEASURING THE VISCOSITY OF A MEDIUM

BACKGROUND OF THE INVENTION

The present invention relates to a method and apparatus for measuring the viscosity of a medium such as coating mass, fish oil, sugar solution, oil, paint, coal sludge, glue and other media with high viscosity, as well as abrasive media, with the aid of a blade pivotably suspended in the medium between two end positions in a measuring zone.

Static transducers of the type mentioned above on the market up till now include a fin or a blade pivotally suspended for example in a pipe containing a medium. These transducers operate with a rapid vibrating motion, and as with rotating transducers there is a heavy working of the medium causing its viscosity to decrease especially in thixotropic media. The use of rotating transducers require that complicated shaft sealings be used for sealing against the medium in question.

BRIEF DESCRIPTION OF THE INVENTION

The object of the present invention is to provide a method and apparatus for measuring viscosity of the kind mentioned wherein the limitations and disadvantages burdening commercial static transducers are eliminated. This object is achieved by the method and apparatus in accordance with the invention having been given the distinguishing features disclosed in the accompanying claims.

By means of the invention there is thus provided a method which advantageously allows measurement of the viscosity of thixotropic media, due to the minor working of the medium by the transducer having an intermittent operational cycle, and being inactive during about 90% of the total time for a stroke. By using a blade describing a reciprocatory, intermittent motion in the mediums the medium is not noticeably worked, and it has time to rest or recover from working between each stroke. As is well known, thixotropic media change their viscosity due to the degree of working. The intermittent operational cycle further contributes to a representative sample of the medium always being in the measuring zone. The transducer has a large measuring range, which can easily be changed by changing the width of the blade, its thickness, stroke, storke rate and current strength to the coil activating it. In contradistinction to rotary viscosity meters, which often have complicated shaft seals, the invention has a static seal of the O-ring type, which is a great advantage from the aspect of complexity, and has prime importance in respect of abrasive and aggressive media.

BRIEF DESCRIPTION OF THE DRAWINGS

The invention will now be described in detail with reference to the accompanying drawing, on which FIG. 1 is a partial, schematic cross section of a viscosity transducer in accordance with the present invention, mounted in a pipe, FIG. 2 is a schematic side view of the optical reading fork illustrated in FIG. 1, FIG. 3 is a schematic perspective view of the functions of reading fork and ray interrupter and FIG. 4 is a plan view of the transducer illustrated in FIG. 1, the blade of which is illustrated with dashed lines between the side walls.

DETAILED DESCRIPTION OF THE PREFERRED EMBODIMENT

A preferred embodiment of a viscosity transducer in accordance with the present invention is illustrated partly in section in FIG. 1, mounted in a pipe 1, the transducer also including a blade 2 pivotably suspended in the medium in the pipe 1. The blade 2 is arranged to pivot with its free end 6 moving between two end positions A and B between two fixed side walls 3 and 4, which may be joined to each other via a crosspiece 7. The area between the side walls 3, 4 defines a measuring zone. A power source, in the form of an electromagnetic system 9 and a plunger coil 20 giving a constant force, is arranged such as to intermittently activate the blade 2 via a suspension shaft 8, so that the blade 2 pivots about a mounting 5 situated between the free end 6 of the blade 2 and the suspension shaft free end 10. The free end of the blade 2 traverses a distance A-B or B-A during a given time. The time for the blade 2 to make this angular stroke about the mounting 5 is a function of the sheer force occurring when the medium in question is pressed out of, or sucked into the measuring zone. In turn, this sheer force is a function of the viscosity of the medium. The viscosity transducer in accordance with the present invention operates according to the sheer force principle. when the blade 2 moves between the fixed side walls 3, 4, the medium is urged away in the direction of its movement while at the same time new medium is sucked into the space between the side wall 3 or 4 and the other side of the blade 2, i.e. a sheer force occurs when the medium is urged out of, or sucked into the measuring zone. The side walls each have a major planar surface which extends perpendicularly to the direction of movement of the blade. The blade itself is also generally planar and its major surfaces extend perpendicularly to the direction of movement of the blade. The electromagnetc system 9 which activates the blade 2 comprises a magnet housing 14 and a plunger coil 20. When current is coupled to the plunger coil 20, the blade 2 is caused to make an angular stroke at a constant force about the mounting point 5. After a measuring stroke is completed the current to the plunger coil 20 is reversed and the blade 2 moves back to its original position. The blade 2 moves at a rate ranging from one stroke per second (1.0 Hz) to one stroke every five seconds (0.2 Hz).

An electronic amplifier evaluation unit, not illustrated in the drawing, measures the time for the stroke A-B and/or B-A with the aid of an optical reading fork 12 containing an IR-light emitting diode 16 (LED) and a detector 17, the gap 15 which is traversed by a beam interrupter 11 attached to the suspension shaft 8, as is schematically illustrated in FIGS. 2 and 3. The amplifier evaluation unit sums five time periods, for example, and generates a mean value thereof to form a representative time for each of the five executed strokes. For each new stroke the first time of the five is subtracted and the new time added, which gives a continuous means value formation of the time for one storke. The system 9 is situated at the free end 10 of the suspension shaft 8, and comprises a solenoid magnet 14 fixed to the housing 13 for coaction with the plunger coil 20 arranged at the free end 10 of the suspension shaft 8, such as to provide the pivoting motion of the blade 2 about the mounting 5. The optical reading fork 12 is also fixed to the housing 13 in the region of the suspension shaft free end 10. Between the mounting 5 and the suspension shaft free end 10 there are mechanical stroke limiting means 18, 19 arranged for arresting the pivoting movement of the suspension shaft 8.

A number of measurements form the basis of the mean time value. The number depends on the time constant selected. This mean time value is presented by the amplifier evaluation unit as a standardized output signal e.g. 0–20 mA or 4–20 mA.

In reality, the time measurement is only made during a portion of the stroke, the beam interrupter 11 interrupting the light beam between the legs of the reading fork 12. The beam interrupter 11 has a width corresponding to about 60% of the total stroke. The first and last parts of the angular stroke are thus not included in the measurement. In this way, possible material deflection and resilience in the mechanical stroke limiting means 18 and 19 are prevented from affecting the length of the measuring distance. In the preferred embodiment the blade 2 has a length measured from the bearing 5 of about 100 mm and a width of about 65 mm. In the region of the mounting 5 the suspension shaft 8 is further sealed against the medium by a static seal 21 of the O ring type.

I claim:

1. A method for measuring the viscosity of a medium with the aid of a pivotally suspended blade which extends into the medium and pivots between first and second end positions, said method comprising the steps of:
   alternately and intermittently pivoting said blade between said first and second end positions by alternately applying constant but opposite forces to said blade, whereby the time it takes for said blade to move between said first and second end positions varies as a function of the viscosity of said medium; and
   measuring the speed at which said blade moves between said first and second end positions, said speed being a function of the viscosity of said medium.

2. The method of claim 1, wherein said blade is pivoted between said first and second end positions at a constant frequency.

3. The method of claim 2, wherein said blade rests at each of said first and second end positions before returning to the other of said first and second end positions.

4. The method of claim 1, wherein one or the other of said opposite forces are substantially continuously applied to said blade so that the time that said blade is moving between said first and second end positions and the time that said blade is in either said first or said second end positions is determined by the viscosity of said medium.

5. The method of claim 1, wherein saqid opposite forces are alternately applied to said blade at a constant frequency and the relative time period that said blade is either moving between said first and second end positions or is stationary at said first or second end position is determined by the viscosity of said medium.

6. The method of claim 1, wherein said blade moves through a measuring zone in said medium defined by first and second end walls located adjacent said first and second end positions, respectively, said measuring zone being opened to said vessel so that said medium is free to flow into and out of said measuring zone, said end walls each having a major planar surface located perpendicular to the direction of movement of said blade, said blade being generally planar in shape with its major surfaces being generally perpendicular to the direction of movement of said blade, whereby a shear force is created by the flow of said medium into and out of said measuring zone as said blade is pivoted between said first and second end positions.

7. The method of claim 6, wherein said measuring zone is further defined by a cross bar connecting respective ends of said end walls.

8. The method of claim 1, wherein said speed is measured by measuring the time it takes for said blade to traverse a distance which is less than the entire distance between said first and second end positions.

9. The method of claim 8, wherein said distance is substantially less than said entire distance between said first and second end positions.

10. The method of claim 9, wherein said distance is approximately 60 percent of the total distance between said first and second end positions and is located approximately centrally between said end positions.

11. Apparatus of measuring the viscosity of the medium comprising:
    a pivotally suspended blade which extends into said medium and pivots between first and second end positions;
    means for alternately and intermittently pivoting said blade between said first and second end positions by alternately applying constant but opposing forces to said blade, where by the time it takes for said blade to move between said first and second end positions varies as a function of the viscosity of said medium; and
    means for measuring the speed at which said blade moves between said first and second end positions, said speed being a function of the viscosity of said medium.

12. The apparatus of claim 11, wherein said pivoting means pivots said blade between said first and second end positions at a constant frequency.

13. The apparatus of claim 12, wherein said blade rests at each of said first and second end positions before returning to the other of said first and second end positions.

14. The apparatus of claim 11, wherein one or the other of said opposite forces are substantially continually applied to said blade so that the time that said blade is moving between said first and second end positions and the time that said blade is either in said first or second end positions is determined by the viscosity of said medium.

15. The apparatus of claim 11 wherein said pivoting means alternately applies said opposite forces to said blade at a constant frequency and the relative time period that said blade is either moving between said first and second end positions or is stationary at said first or second end position is determined by the viscosity of said medium.

16. The apparatus of claim 11, wherein said blade moves through a measuring zone in said medium defined by first and second end walls located adjacent said first and second end positions, respectively, said measuring zone being opened to said vessel so that said medium is free to flow into and out of said measuring zone, said end walls each having a major planar surface located perpendicular to the direction of movement of said blade, said blade being generally planar in shape with its major surface being generally perpendicular to the direction of movement of said blade, whereby sheer forces created by the flow of said medium into and out of said measuring zone as said blade is pivoted between said first and second end positions.

17. The apparatus of claim 16, wherein said measuring zone is further defined by a cross bar connecting respective ends of said end walls.

18. The apparatus of claim 11, wherein said measuring means measures the speed of said blade by measuring the time it takes for said blade to traverse a distance which is less than the entire distance between said first and second end positions.

19. The apparatus of claim 18, wherein said distance is substantially less than said entire distance between said first and second end positions.

20. The apparatus of claim 19, wherein said distance is approximately sixty percent (60%) of the total distance between said first and second end positions and is located approximately centrally between said end positions.

21. The apparatus of claim 11, wherein said pivoting means comprises an electromagnetic system including a solenoid magnet and a plunger coil, said plunger coil being coupled to a suspension shaft connected to one end of said blade, and means for applying a current of constant but alternating magnitude to said coil so as to cause said coil to oscillate with reference to said solenoid magnet and thereby to cause said blade to pivot between said first and second end positions.

22. The apparatus of claim 11, wherein said measuring means includes an optical reading fork which includes a light emitting diode and a detector located on opposite sites of a gap of the reading fork and a beam interrupter coupled to one end of said pivoting blade so as to oscillate with said pivoting blade, said beam interrupter moving within said gap of said reading fork so as to alternately permit and prevent the light flow from said light emitting diode to reach said beam detector.

23. The apparatus of claim 11, wherein said medium is located in a fluid vessel, said blade extends into said fluid vessel, said pivoting means is located in a housing external of said fluid vessel and a suspension shaft couples said pivoting means to said blade, said suspension shaft being sealed with the use of an O-ring to prevent said medium from leaking from said vessel into said housing.

24. A method for measuring the viscosity of a medium with the aid of a pivotally suspended blade which extends into the medium and pivots between first and second end positions, said method comprising the steps of:
    alternately and intermittently pivoting said blade between said first and second end positions by alternately applying opposite forces to said blade, whereby the time it takes for said blade to move between said first and second end positions varies as a function of the viscosity of said medium, said blade resting at each of said first and second end positions before returning to the other of said first and second end positions, said blade being operated cyclically and being inactive during about at least 90% of the total time of any given stroke associated with the blade; and
    measuring the speed at which said blade moves between said first and second end positions, said speed being a function of the viscosity of said medium.

25. Apparatus of measuring the viscosity of the medium comprising:
    a pivotally suspended blade which extends into said medium and pivots between first and second end positions;
    means for alternately and intermittently pivoting said blade between said first and second end positions by alternately applying opposing forces to said blade, whereby the time it takes for said blade to move between said first and second end positions varies as a function of the viscosity of said medium, said blade resting at each of said first and second end positions before returning to the other of said first and second end positions and said blade being operated cyclically and said means for alternately and intermittently pivoting said blade being effective for keeping said blade inactive for at least about 90% of any given cycle of said blade; and
    means for measuring the speed at which said blade moves between said first and second end positions, said speed being a function of the viscosity of said medium.

* * * * *